US006420577B1

(12) United States Patent
Reaney et al.

(10) Patent No.: US 6,420,577 B1
(45) Date of Patent: Jul. 16, 2002

(54) METHOD FOR COMMERCIAL PREPARATION OF CONJUGATED LINOLEIC ACID

(75) Inventors: Martin J. Reaney; Ya-Dong Liu; Neil D Westcott, all of Saskatoon (CA)

(73) Assignee: Her Majesty the Queen in right of Canada, as represented by the Minister of Agriculture, Ottawa (CA)

( * ) Notice: Subject to any disclaimer, the term of this patent is extended or adjusted under 35 U.S.C. 154(b) by 0 days.

(21) Appl. No.: 09/451,710

(22) Filed: Dec. 1, 1999

(51) Int. Cl.$^7$ .......................... C07C 51/347; C11B 3/00

(52) U.S. Cl. ....................... 554/126; 554/554; 554/155; 554/156; 554/157; 554/158

(58) Field of Search ................................ 554/154, 155, 554/124, 156–157, 158, 126, 208

(56) References Cited

U.S. PATENT DOCUMENTS

| | | | | | |
|---|---|---|---|---|---|
| 2,242,230 | A | | 5/1941 | Burr | 260/398 |
| 2,343,644 | A | * | 3/1944 | Cawley | 260/405.6 |
| 2,350,583 | A | | 6/1944 | Bradley | 260/405.6 |
| 2,389,260 | A | | 11/1945 | Kirschenbauer | 260/405.6 |
| 4,164,505 | A | * | 8/1979 | Krajca | 260/405 |
| 4,376,711 | A | | 3/1983 | Shaub | 252/32.7 E |
| 4,381,264 | A | | 4/1983 | Struve | 260/405.6 |
| 4,393,043 | A | | 7/1983 | Koulbanis | 424/59 |
| 5,053,534 | A | | 10/1991 | Cosgrove | 562/509 |
| 5,070,104 | A | | 12/1991 | Pariza | 514/549 |
| 5,194,640 | A | | 3/1993 | Cosgrove | 554/126 |
| 5,428,072 | A | | 6/1995 | Cook | 514/560 |
| 5,430,066 | A | | 7/1995 | Cook | 514/558 |
| 5,504,114 | A | | 4/1996 | Cook | 514/558 |
| 5,554,646 | A | | 9/1996 | Cook | 514/560 |
| 5,585,400 | A | | 12/1996 | Cook | 514/560 |
| 5,674,901 | A | | 10/1997 | Cook | 514/558 |
| 5,693,216 | A | * | 12/1997 | Hart et al. | 208/188 |
| 5,760,083 | A | | 6/1998 | Cook | 514/560 |
| 5,770,247 | A | | 6/1998 | Satter | 426/2 |

FOREIGN PATENT DOCUMENTS

| | | | | |
|---|---|---|---|---|
| GB | 1140193 | * | 10/1969 | 554/155 |
| GB | 1282474 | * | 10/1969 | 554/208 |
| GB | 1391906 | * | 5/1972 | 554/155 |

OTHER PUBLICATIONS

Baileys Fats and Oils, vol. 4, fifth Edition, Edible Oil & Fat Products: Processing Technology, 1995.*

Bailey' Fats and Oils, vol. 4, 5th ed., Edible Oils & Fat Products: Processing Technology, pp. 56–57, 1996.*

See Separation of Fatty components by solid phase absorption, Cot, et al, ibib and abstract, AN 1993:430346 CAPLUS, 1993.

* cited by examiner

*Primary Examiner*—Deborah D. Carr

(57) ABSTRACT

Methods for simultaneous saponification and quantitative isomerization of glyceride oils containing interrupted double bond systems, with alkali in water to yield soaps with conjugated double bond systems are disclosed. Novel methods of hydrolysis of the soap product with acid to form fatty acid-water emulsions and the breaking of those emulsions are also disclosed. The preferred embodiment uses a vegetable oil rich in linoleic acid such as sunflower or safflower oil, potassium hydroxide, phosphoric acid to neutralize the soaps, and an emulsion breaking compound which can include ethanol or other monohydric alcohol, tannins (either hydrolysable or condensed tannin) or polyethylene glycol. The reaction forms positional and geometric isomers of conjugated linoleic acid and the preferred isomer mixture is controlled by a combination of agitation, precisely controlled heating and rapid initiation and termination of the reaction. The reaction product composition may be enriched by crystallization.

10 Claims, 6 Drawing Sheets

METHOD FOR COMMERCIAL PREPARATION OF CONJUGATED LINOLEIC ACID

FIELD OF INVENTION

This invention relates to an improved process for preparation of conjugated linoleic acid (CLA) from oils rich in linoleic acid, which overcomes problems with an intractable emulsion that occurs between CLA and water by treatment with either an alcohol or polyethylene glycol or a tannin. The reaction is also unique in that it allows the control of the production of positional isomers in the conjugated linoleic acid. The process by-product stream is usable directly as a fertilizer that limits waste disposal costs.

BACKGROUND OF THE INVENTION

Conjugated linoleic acid is the trivial name given to a series of eighteen carbon diene fatty acids with conjugated double bonds. Applications of conjugated linoleic acids vary from treatment of medical conditions such as anorexia (U.S. Pat. No. 5,430,066) and low immunity (U.S. Pat. No. 5,674,901) to applications in the field of dietetics where CLA has been reported to reduce body fat (U.S. Pat. No. 5,554,646) and to inclusion in cosmetic formulae (U.S. Pat. No. 4,393,043).

CLA shows similar activity in veterinary applications. In addition, CLA has proven effective in reducing valgus and varus deformity in poultry (U.S. Pat. No. 5,760,083), and attenuating allergic responses (U.S. Pat. No. 5,585,400). CLA has also been reported to increase feed conversion efficiency in animals (U.S. Pat. No. 5,428,072). CLA-containing bait can reduce the fertility of scavenger bird species such as crows and magpies (U.S. Pat. No. 5,504, 114).

Industrial applications for CLA also exist where it is used as a lubricant constituent (U.S. Pat. No. 4,376,711). CLA synthesis can be used as a means to chemically modify linoleic acid so that it is readily reactive to Diels-Alder reagents (U.S. Pat. No. 5,053,534). In one method linoleic acid was separated from oleic acid by first conjugation then reaction with maleic anhydride followed by distillation (U.S. Pat. No. 5,194,640).

Conjugated linoleic acid occurs naturally in ruminant depot fats. The predominant form of CLA in ruminant fat is the cis,trans-9,11-octadecadienoic acid which is synthesized from linoleic acid in the rumen by micro-organisms like *Butryvibrio fibrisolvens*. The level of CLA found in ruminant fat is in part a function of dietary cis, cis-9,12-octadecadienoic acid and the level of CLA in ruminant milk and depot fat may be increased marginally by feeding linoleic acid (U.S. Pat. No. 5,770,247).

CLA may also be prepared by any of several analytical and preparative methods. Pariza and Ha "pasteurized" a mixture of butter oil and whey protein at 85° C. for 5 minutes and noted elevated levels of CLA in the oil (U.S. Pat. No. 5,070,104). CLA produced by this mechanism is predominantly a mixture of cis,trans-9,11-octadecadienoic acid and trans,cis-10,12-octadecadienoic acid.

CLA has also been produced by the reaction of soaps with strong alkali bases in molten soaps, alcohol, and ethylene glycol monomethyl ether (U.S. Pat. Nos. 2,389,260; 2,242, 230 & 2,343,644). These reactions are inefficient as they require the multiple steps of formation of the fatty acid followed by production of soap from the fatty acids, and subsequently increasing the temperature to isomerize the linoleic soap. The CLA product is generated by acidification with a strong acid (sulfuric or hydrochloric acid) and repeatedly washing the product with brine or $CaCl_2$.

CLA has been synthesized from fatty acids using $SO_2$ in the presence of a sub-stoichiometric amount of soap forming base (U.S. Pat. No. 4,381,264). The reaction with this catalyst produced predominantly the all trans configuration of CLA.

Efficient synthesis of cis,trans-9,11-octadecadienoic from ricinoleic acid has been achieved (Russian Patent 2,021, 252). This synthesis, although efficient, uses expensive elimination reagents such as 1,8-diazobicyclo-(5,4,0)-undecene. For most applications the cost of the elimination reagent increases the production cost beyond the level at which commercial production of CLA is economically viable.

Of these methods alkali isomerization of soaps is the least expensive process for bulk preparation of CLA isomers, however, the use of either monohydric or polyhydric alcohols in alkali isomerization of CLA can be problematic. Lower alcohols are readily removed from the CLA product but they require the production facility be built to support the use of flammable solvents. Higher molecular weight alcohols and polyhydric alcohols are considerably more difficult to remove from the product and residual levels of these alcohols (e.g. ethylene glycol) may not be acceptable in the CLA product.

Water may be used in place of alcohols in the production of CLA by alkali isomerization of soaps (U.S. Pat. Nos. 2,350,583 and 4,164,505). When water is used for this reaction it is necessary to perform the reaction in a pressure vessel whether in a batch (U.S. Pat. No. 2,350,583) or continuous mode of operation (U.S. Pat. No. 4,164,505). The process for synthesis of CLA from soaps dissolved in water still requires a complex series of reaction steps. Bradley and Richardson (*Industrial and Engineering Chemistry February* 1942 vol 34 no2 237–242) were able to produce CLA directly from soybean triglycerides by mixing sodium hydroxide, water and oil in a pressure vessel. Their method eliminated the need to synthesize fatty acids and then form soaps prior to the isomerization reaction. However, they reported that they were able to produce an oil with up to 40 percent CLA. Quantitative conversion of the linoleic acid in soybean oil to CLA would have produced a fatty acid mixture with approximately 54 percent CLA.

Commercial conjugated linoleic acid often contains a mixture of positional isomers that may include trans,cis-8, 10-octadecadienoic acid, cis,trans-9,11-octadecadienoic acid, trans,cis-10,12-octadecadienoic acid, and cis,trans-11, 13-octadecadienoic acid (Christie, W. W., G. Dobson, and F. D. Gunstone, (1997) "Isomers in commercial samples of conjugated linoleic acid." J. Am. Oil Chem. Soc. 74,11, 1231). Sebedio et al. (Inform Volume 10. No.5) prepared highly enriched CLA acids isomers and studied their effects on rat tissue lipids. They reported that virtually all of the biological activity of the mixed CLA isomers could be attributed to trans,cis-10,12-octadecadienoic acid while very little activity could be ascribed to the cis,trans-9,11-octadecadienoic acid isomer. A commercial reaction to prepare CLA should therefore produce an enriched fraction of trans,cis-10,12-octadecadienoic acid.

The present invention describes a method of production of CLA using water as a reaction medium and a vegetable oil containing more than 60% linoleic acid. The reaction in water produces several isomers but the isomer ratio is controlled by the addition of modifiers and reaction kinetics.

The reaction products may be specifically enriched in trans, cis-10,12-octadecadienoic acid the most active CLA isomer in many assays of CLA activity. The catalytic reaction in alkali is uniquely useful in producing deuterium and tritium labelled isomers of CLA that is achieved by conducting the reaction in deuterated or tritiated water. Isotopically labelled CLA is useful in metabolic studies of CLA metabolism.

When this product is quantitatively converted to CLA it forms an intractable emulsion that is not readily broken using conventional techniques of resolving emulsions such as freezing, heating and centrifugation. Other researchers have used conventional methods to wash and dehydrate the CLA isomers with solutions of $CaCl_2$ when the CLA content of the fatty acids is below 50%. We have found that these methods are not suitable for breaking emulsions caused by solutions that contain over 60% CLA.

SUMMARY OF THE INVENTION

In the present invention the quantitative production of CLA from linoleic acid rich oils is achieved by hydrolysis and isomerization with base in a single step reaction in water, deuterated water or tritiated water and the physical separation of the fatty acids from the water or isotopically labelled water after isomerization. A preferred embodiment entails the addition of 45% aqueous potassium hydroxide as the base/catalyst; thereafter, the reaction mixture is neutralized by a strong acid, with 70% $H_3PO_4$ being preferred. The selection of $H_3PO_4$ as the acid and KOH as the base allow the aqueous salt solution to be disposed of in surface applications such as a liquid or solid fertilizer. The neutralized reaction mixture forms an emulsion that can be separated only by the addition of demulsifiers. The demulsifier used to break the emulsion formed by CLA and water must be inexpensive and suitable for the production of food, cosmetic and medicinal products. It has now been found that the emulsions between CLA and water can be broken using polyethylene glycol, ethanol or other monohydric alcohol or tannin (hydrolysable or condensed) or fulvic acid or humic acid. The reaction can also be controlled to minimize the production of undesirable isomers. The major element of control is through the vigorous agitation of the CLA reaction mixture during synthesis. Refining of CLA with solid phase refining methods is also contemplated. The partial enrichment and concentration of specific CLA isomers using crystallization from organic solvent is also contemplated.

This invention provides a process for producing a conjugated linoleic acid-rich fatty acid mixture comprising reacting a linoleic acid-rich oil with a base in the presence of a catalytic amount of said base in an aqueous medium at a temperature above 170° C., and separating said conjugated linoleic acid-rich fatty acid mixture from said aqueous medium.

DETAILED DESCRIPTION OF THE INVENTION

Figure 1A:
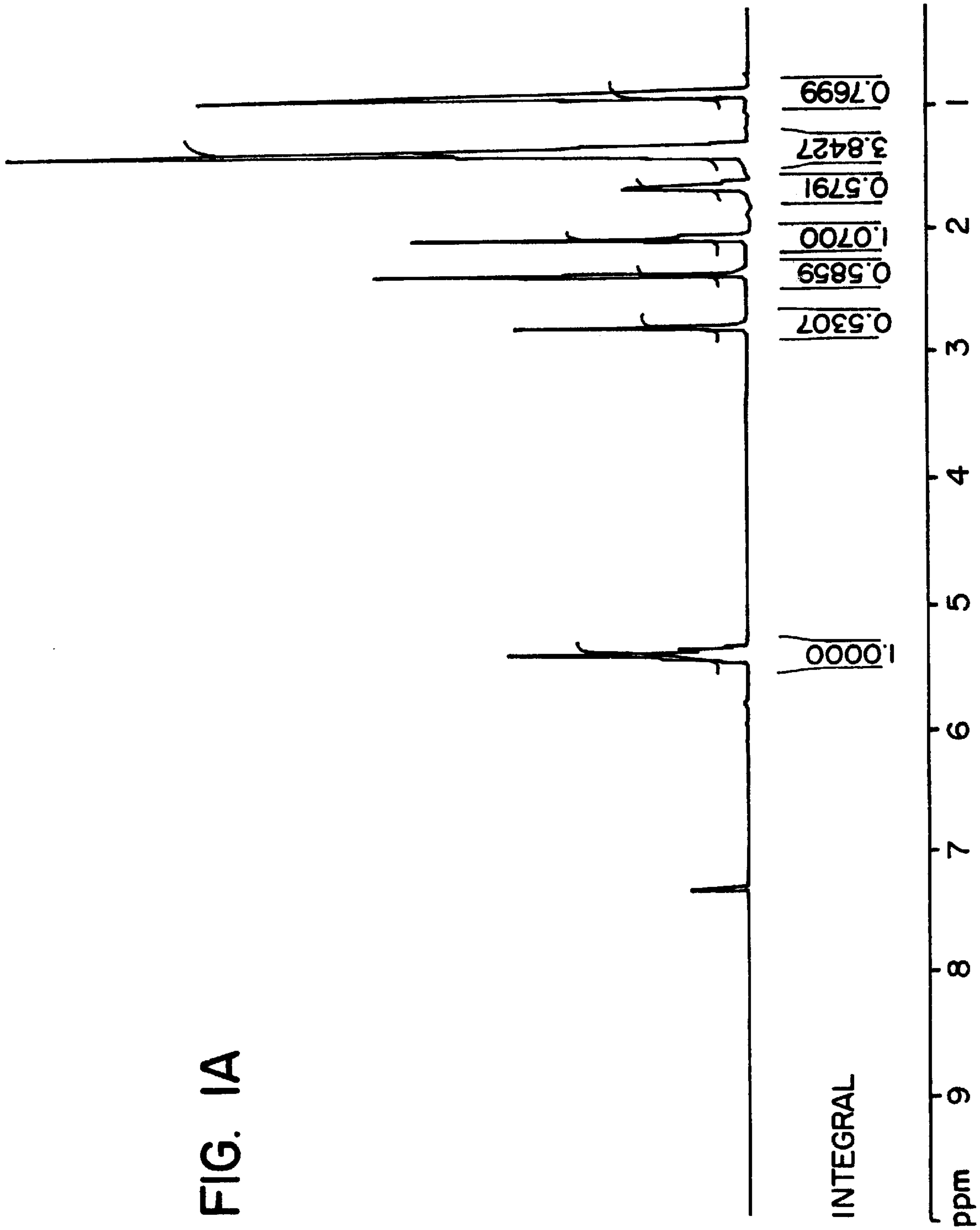
FIG. 1A is the proton spectrum of a standard of cis,trans-9,11-octadecadienoic acid.

The disclosed process quantitatively converts linoleic acid rich oils to a mixture of fatty acids containing CLA. The process involves blending a vegetable oil rich in linoleic acid or a partial glyceride of such a vegetable oil with 1–6 moles of base, part of which acts as a reactant and part of which acts as a catalyst, and 10 to 100 moles of water per mole of hydrolysable acyl groups. The vegetable oil may include cottonseed, cucumber, grape seed, corn, safflower, soybean, sunflower or walnut oil or any other oil, wax or ester that is rich in linoleic acid. The reaction will proceed if about 1 mole of a base such as sodium metal, sodium hydroxide, sodium alkoxylate, potassium metal, potassium hydroxide or potassium alkoxylate is used as reactant and up to 5 moles are used as the catalyst. The least expensive alkali that does not represent a disposal problem is 45% aqueous potassium hydroxide. Furthermore, metallic alkali produces explosive hydrogen gas when added to water and metal alkoxylates are flammable. These factors support the use of aqueous potassium hydroxide as the preferred catalyst/reactant. The reaction proceeds at temperatures above 170° C. and the reaction accelerates with increases in temperature. Preferred embodiments involve performing the reaction above 180° C. As the reactor contains water it is necessary to confine the reaction in a sealed pressure vessel.

The reaction proceeds very rapidly at temperatures above 200° C. and the reaction is sensitive to small changes in temperature. The reaction vessel used for the process must have a homogeneous temperature or the reaction will not proceed uniformly. Homogeneous temperature is achieved by vigorous stirring or turbulent flow conditions. In a preferred embodiment the reaction mixture is prepared with a sub-stoichiometric level of KOH and heated to the reaction temperature. The reactor is then charged with the catalyst under pressure to begin the reaction. Using this method the reaction starts in the time required to add the catalyst. The reaction is terminated either through the addition of acid or through the rapid cooling of the reaction mixture to prevent the further formation of positional isomers.

After the reaction is complete the mixture is cooled to 90–100° C. for separation of the reaction by-products. Acid is added to the reaction mixture to hydrolyse the soaps in the reactor. It is preferred to bring the pH of the contents of the reactor to pH 4 or less through the addition of either a mineral or organic acid. Acids that may be used include, but are not limited to, hydrochloric acid, sulfuric acid, phosphoric acid and citric acid. It is found that the use of sulfuric and hydrochloric acid is problematic in that these strong acids may react chemically with the CLA during separation. The preferred embodiment of this invention involves the use of phosphoric acid or citric acid to hydrolyse the soaps. When phosphoric acid is used the waste solution can be neutralized and used as a surface applied fertilizer and there are no disposal costs for discarding this product. The hydrolysed soaps form an intractable emulsion in the reactor at 100° C. The emulsion can readily be broken by the addition of one of several synthetic commercial demulsifiers which, however, are not acceptable for use in food and cosmetic systems. This invention includes the use of several natural compounds and one synthetic compound as demulsifiers. Ethanol was found to act as a demulsifier when added to the reaction mixture at concentrations between 2 and 10 percent. Ethanol tended to boil at temperatures required for phase separation and thus ethanol was not a preferred alcohol for phase separation. Other higher molecular weight alcohols like n-butanol also effected separation of the fatty acid aqueous emulsion without the problem of the tendency to boil. These alcohols tended to partition into the fatty acid phase and it was found necessary to strip these solvents from the fatty acid after processing. Polyethylene glycol (PEG) of widely different molecular weights was effective in separating the emulsion when added at concentrations between 1 and 10 percent of the reaction mixture. Although polyethylene glycol was effective it accumulated to a concentration of between 1 and 7 percent in the fatty acid phase. This high concentration of PEG could not be effectively removed from the fatty acids by water washing or washing with brine. However, as part of the embodiment of this invention we discovered that PEG could be removed from the fatty acid layer by washing the fatty acids with 70 percent aqueous phosphoric acid at between 85 and 110° C. We found that the emulsion breaking properties and phase partitioning properties of PEG molecules of widely different molecular sizes (PEG 300 and PEG 8,000) to be the same.

Surprisingly naturally occurring tannins including tannic acid (a hydrolysable tannin) and quebracho tannin (a condensed tannin) were also found to effectively separate the emulsion of fatty acids and water. Tannins have previously been shown to be effective at breaking emulsions of crude petroleum and water; for example, U.S. Pat. No. 5,693,216 reveals methods and compositions for breaking oil and water emulsions in crude oil processing operations using a copolymer of tannin and a cationic monomer, but to our knowledge tannins have never been used to effect the separation of emulsions of fatty acids and aqueous solutions.

Figure 1B:
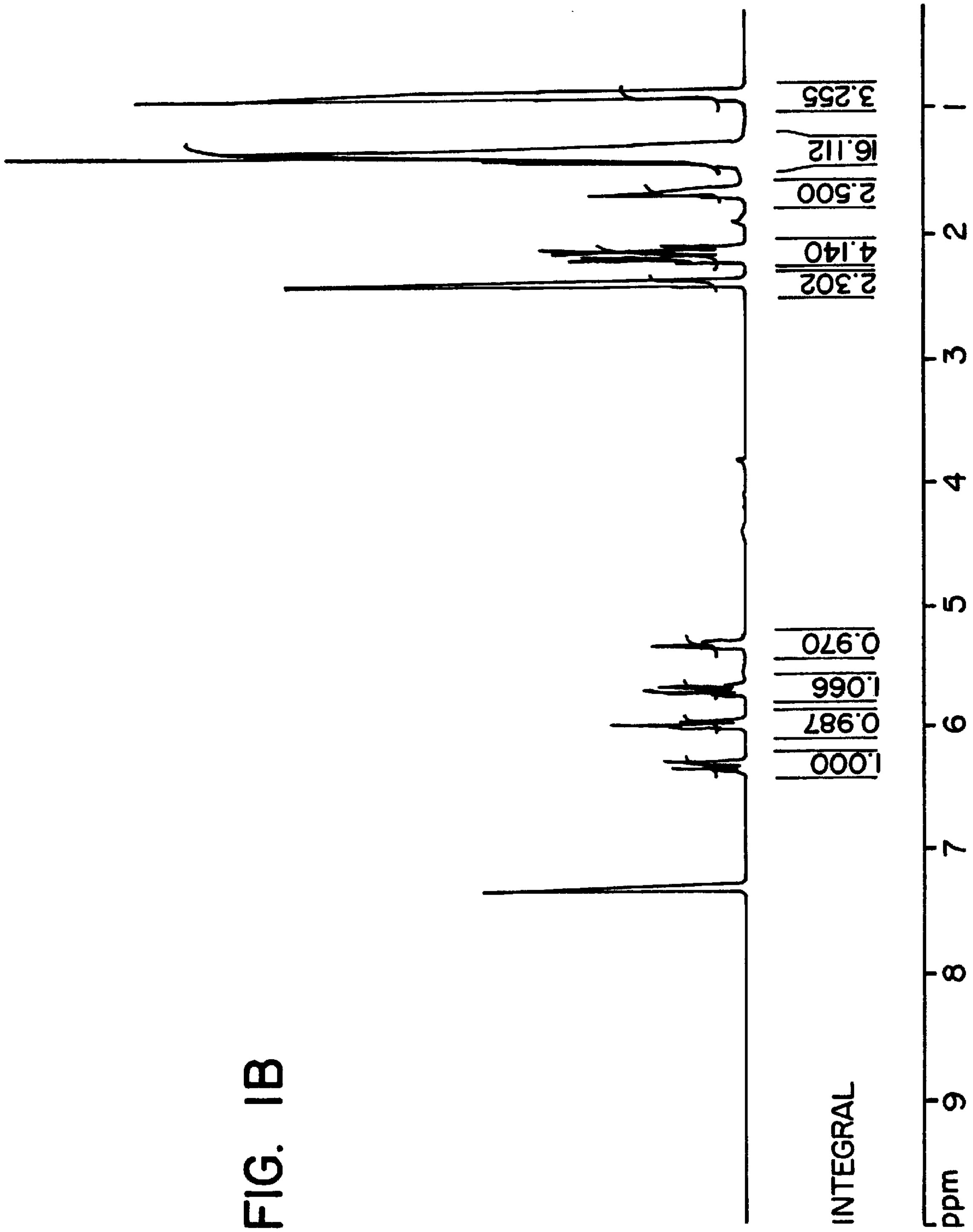
FIG. 1B is the proton spectrum of linoleic acid.

Reaction progress was determined by proton ($^1$H-NMR-400 MHz) nuclear magnetic resonance spectroscopy. FIG. 1A is the proton spectrum of a standard of cis,trans-9,11-octadecadienoic acid while FIG. 1B is the spectrum of linoleic acid. As may be concluded from FIG. 1 the disappearance of interrupted methylene signal at 2.8 PPM is a measure of the disappearance of linoleic acid (FIG. 1). The concentration of total fatty acid is proportional to the alpha methylene proton peak which is located at 2.2 PPM. The initial linoleic acid content was determined from $^1$H-NMR spectra by dividing the integrated area of the peak at 2.8 PPM of the vegetable oil by the integrated area of the peak at 2.2 PPM. The linoleic acid content of subsequent samples was determined by the same method employed on the reacted fatty acids.

Figure 2A:
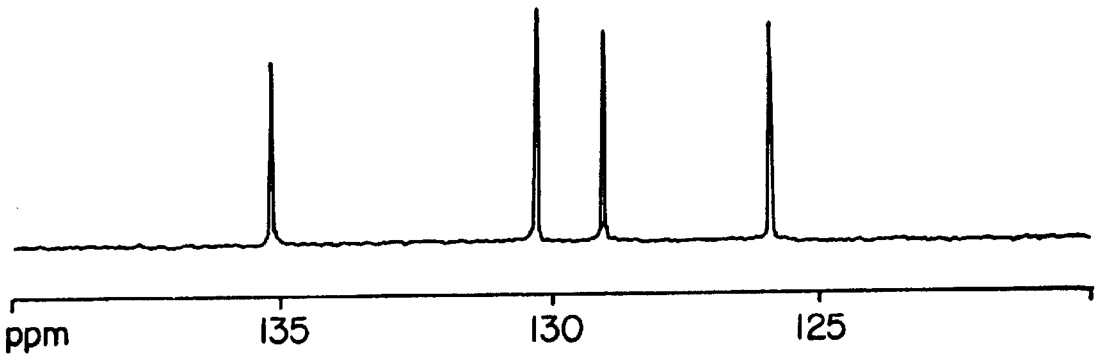
FIGS. 2A–D are carbon 13 NMR traces for selected octadecadienoic acid isomers.
Figure 2B:
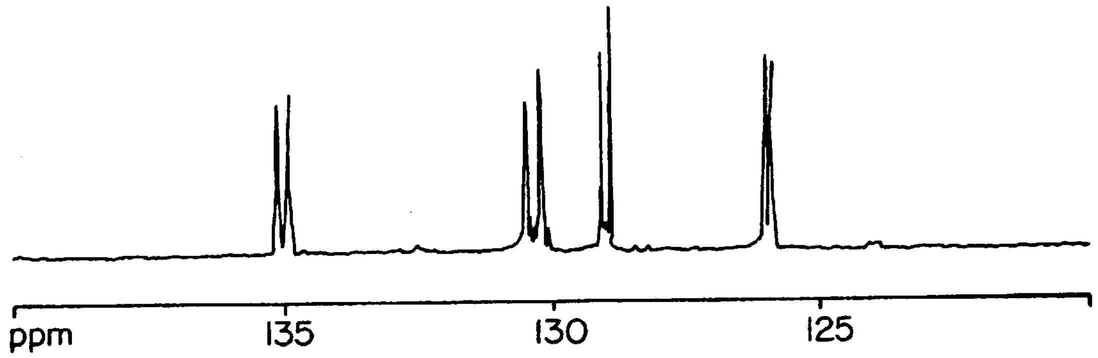
Figure 2C:
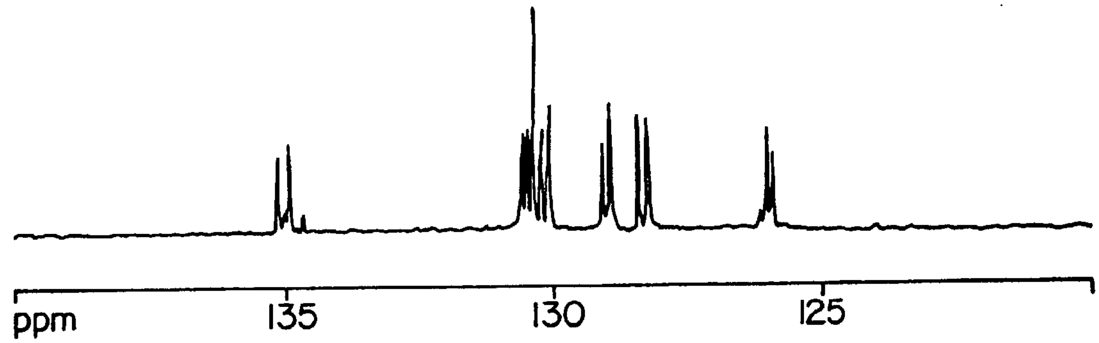
Figure 2D:
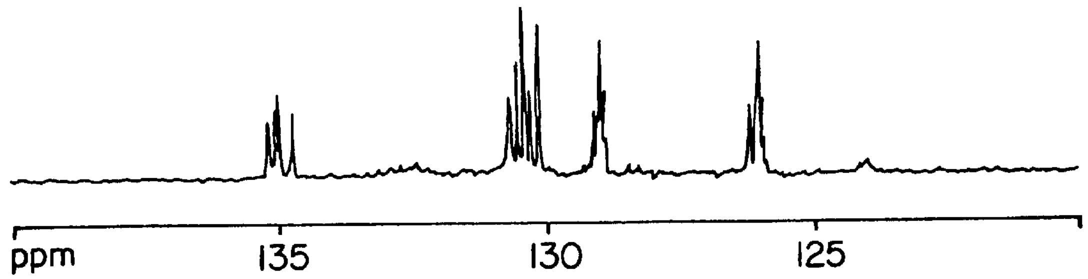

Isomer composition of the fatty acids was determined by carbon 13($^{13}$C-NMR-100 MHz) nuclear magnetic resonance spectroscopy. A standard of cis,trans-9,11-octadecadienoic acid gave four peaks in the $^{13}$C-NMR spectrum that were attributed to the olefinic carbons C-9, C-10, C-11 and C-12 at 130.31, 129.10, 125.94 and 135.22 PPM respectively (FIG. 2A) while mixtures known to contain only cis,trans-9,11-octadecadienoic acid and trans,cis-10,12-octadecadienoic acid gave pairs of peaks in each region (FIG. 2B). The deduced assignment for trans,cis-10,12-octadecadienoic acid olefinic carbons C-10, C-11, C-12 and C-13 was 134.94, 126.07, 128.99 and 130.12 PPM respectively. $^{13}$C-NMR spectra of samples containing trans,cis-8,10-octadecadienoic acid, cis,trans-9,11-octadecadienoic acid, trans,cis-10,12-octadecadienoic acid and cis,trans-11,13-octadecadienoic acid gave quadruple peaks clustered at 130, 129, 125.6 and 135 PPM (FIG. 2C). We found that the quadruple peaks located around 135 PPM were better suited for analysis of isomer composition than other peaks as they were better separated (FIG. 2C).

EXAMPLES

Example 1

Simultaneous Hydrolysis and Isomerization of Sunflower Oil to CLA Followed by Washing, Dehydrating and Refining the CLA with PEG 300

To commercial sunflower oil (275 mL) and water (121 mL) were added KOH (45% w/w, 204 mL). The resulting reaction mixture was heated at 215° C. (reactor pressure: 175 psi) for 4 hours in a one liter reactor with vigorous agitation. After cooling to room temperature, the reaction mixture was transferred to a two liter beaker, acidified with $H_3PO_4$ (85%, 204 mL), and PEG 300 was added to the mixture at 5% by weight. The resulting mixture was heated for 0.5 h at 95° C. After standing for a further 0.5 hours at 95° C., the top CLA layer was removed, washed with $H_3PO_4$ (85%, 30 mL) at 95° C. for 30 minutes to remove excess PEG and water. The upper CLA layer was removed. The CLA product contained less than 0.1% water and less than 0.0125% PEG as determined by the method of Muir et al., 1998. The quantitative conversion of linoleic acid to CLA was confirmed by $^1$H-NMR as described above.

Example 2–8

Simultaneous Hydrolysis and Isomerization of Sunflower Oil to CLA Followed by Washing, Dehydrating and Refining the CLA with Tannic Acid or Quebracho Tannin To commercial sunflower oil (275 mL) and water (121 mL) were added KOH (45% w/w, 204 mL). The resulting reaction mixture was heated at 215° C. (reactor pressure: 175 psi) for 6 hours in a one liter reactor with vigorous agitation. After cooling to room temperature, the reaction mixture was transferred to a two liter beaker, acidified with $H_3PO_4$ (85%, 204 mL), and tannic acid added accordingly (See Table 1). The resulting mixture was heated for 2.5 h at 105–110° C. After standing for 0.5 hours 95° C., the upper CLA layer was removed, washed with $H_3PO_4$ (85%, 30 mL), and heated at 95° C. for 30 minutes. The dried CLA layer was separated (See Table 1).

TABLE 1

Separation of CLA emulsions with tannic acid

| Example | Tannin (%, w/w oil) | Tannin (gram) | CLA (mL) | Water (mL) |
|---|---|---|---|---|
| 2 | 8* | 20 | 240 | 100 |
| 3 | 0.8* | 2 | 235 | 0 |
| 4 | 0.1* | 0.25 | 210 | 0 |
| 5 | 0.02* | 0.025 | 205 | 0 |
| 6 | 0.1* | 0.25 | 160 | 100 |
| 7 | 0.8** | 2 | 240 | 0 |
| 8 | 0.8** | 2 | 240 | 100 |

*Tannic acid
*Quebracho tannin

Note:
1: Theoretic yield of CLA is 250 mL for these reactions.

Examples 9–18

Simultaneous Hydrolysis and Isomerization of Sunflower Oil to CLA at Elevated Pressure Using Lower Concentrations of Potassium Hydroxide In a chemical reaction the base performs three discrete functions; hydrolyses the glycerides, reacts with water and fatty acids to produce soaps, and catalyses the isomerization reaction. During the hydrolysis of ester linkages much of the alkaline base is consumed in the formation of soaps. It is only the residual base that remains after the formation of soaps is capable of catalysing the isomerization of linoleic acid to CLA. In previous studies of CLA production in water researchers reported using large excesses of alkali to produce CLA (U.S. Pat. No. 2,350,583). Surprisingly, our research shows that the isomerization reaction may be driven by small excess over stoichiometric addition of KOH. Table 2 shows the conversion of CLA based on standard reaction conditions of example 1 with the addition of various concentrations of aqueous KOH at different reaction temperatures. In these reactions it was possible to obtain a quantitative conversion of linoleic acid to CLA with only a small excess of KOH if the temperature was raised or reaction time increased.

TABLE 2

Production of CLA with different amounts of added base.

| Example | Sunflower oil (mL) | 45% KOH (mL) | Temperature (° C.) | Conversion (%) |
|---|---|---|---|---|
| 9 | 275 | 102 | 210 | 38 |
| 10 | 275 | 102 | 216 | 62 |
| 11 | 275 | 102 | 226 | 86 |
| 12 | 275 | 122 | 210 | 72 |
| 13 | 275 | 122 | 227 | 100 |
| 14 | 275 | 143 | 210 | 85 |
| 15 | 275 | 143 | 224 | 100 |
| 16 | 275 | 163 | 213 | 92 |
| 17 | 275 | 163 | 224 | 100 |
| 18 | 275 | 204 | 210 | 100 |

Example 19

Refining and Enrichment of CLA by Fractional Distillation

As a counter example, high temperature distillation was used to refine CLA and produce a product free of color. Two hundred grams of fatty acids containing 64% CLA, produced as described in example 1 and boiling chips were placed in a 500 mL round bottomed flask with a ground glass fitting and the flask was placed in an electric heating mantle. A 20 mm×470 mm Vigreaux column was inserted in the flask and the column was fitted with a distillation head that incorporated a thermometer for measuring distillate temperature. The Vigreaux column was insulated by a 0.25 cm layer of glass wool held in place by aluminum foil. The apparatus was completed by the addition of a vacuum adapter and 250 mL receiving flask also with ground glass fittings. Vacuum of approximately 100 mm was applied using a Welch Duoseal Vacuum pump, Model 1400. The temperature of the distillate was monitored throughout the procedure. The distillate was removed in three stages determined by boiling temperature. The first stage 40 mL was removed between 222 and 226° C. and was found to be a colorless liquid that readily crystallized at room temperature. The crystalline material was determined to be mostly palmitic acid. The second stage of 125 mL was removed between 226 and 232° C. consisted of an enriched CLA product. The temperature of boiling increased to 245° C. and an additional 10 mL of material distilled. Thereafter the distillation was terminated.

Figure 3:
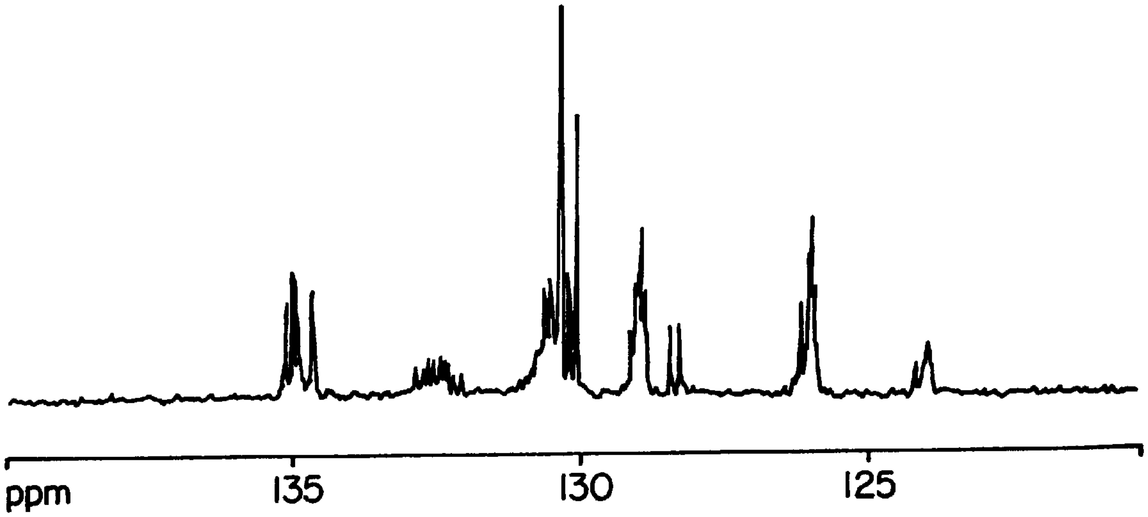
FIG. 3 is a trace of carbon NMR of the products of distillation above 226° C.

Carbon NMR of the products of distillation at temperatures above 226° C. were found to contain a series of CLA isomers with peaks located at 132.5 and 124 PPM (FIG. 3). These peaks reflect the formation of undesirable CLA products of unknown biological activity. Distillation was not an appropriate method of refining CLA.

Example 20

Refining CLA Enriched Fatty Acids

Figure 4:
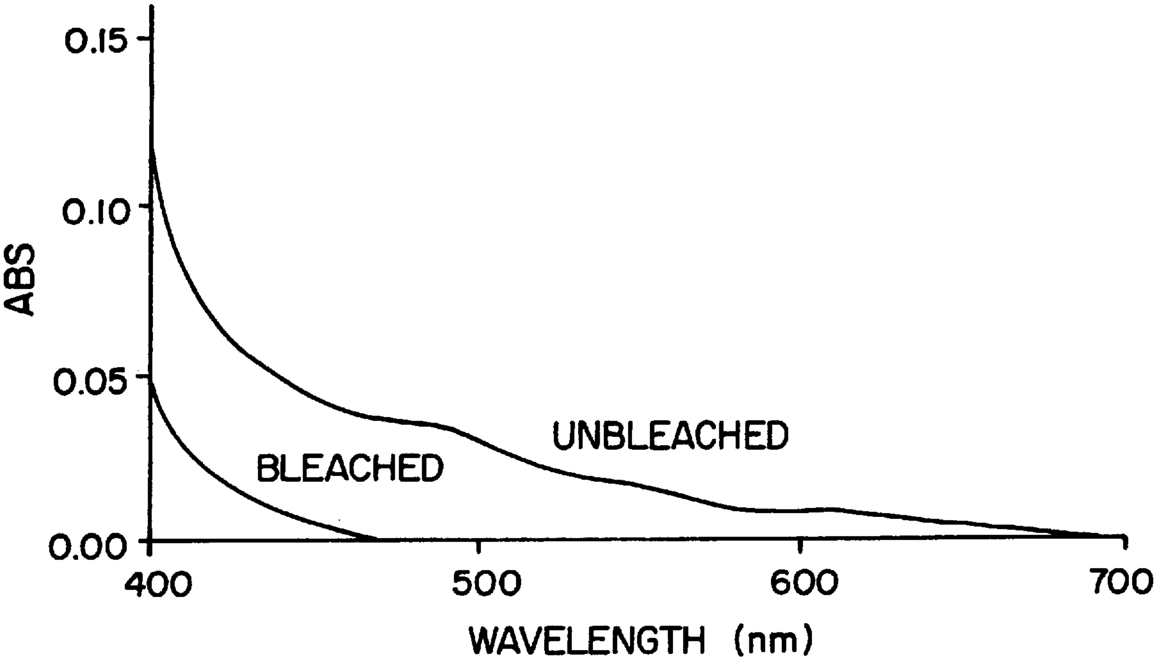
FIG. 4 is a a graph illustrating the visible spectra of bleached and unbleached CLA enriched fatty acids.

The fatty acids produced by all of the methods mentioned above have a straw yellow color and contain some metal ions as determined by inductively coupled plasma spectrometry (Table 3). The yellow color detracts from marketability and the metal ions may cause the material to be unstable. One thousand grams of fatty acid produced as described in example 1 was heated under vacuum in an agitated sealed vessel at 70° C. and 10 grams of bleaching clay (Supreme 120 FF), was added. The mixture was continuously stirred and heated to 105° C., under vacuum, for 30 minutes. When the temperature of the mixture had decreased to 60° C., the vacuum was released. The mixture was then filtered through a Celite filter bed. A comparison of the visible spectra of the two samples is given in FIG. 4 to show the removal of color.

TABLE 3

Metals in reaction mixture and refined oils

| Sample* | Si | Na | K | Pb | Sn | Al | B | Ca | Mg | Sb |
|---|---|---|---|---|---|---|---|---|---|---|
| Mixed | 12 | 476 | 1012 | 12 | 80 | 20 | 52 | 0 | 1 | 33 |
| Bleached | 0 | 2 | 28 | 0 | 0 | 0 | 3 | 1 | 0 | 0 |
| Distilled | 4 | 1 | 4 | 0 | 0 | 0 | 0 | 5 | 0 | 0 |

*reaction mixture contains caustic, sunflower oil and water as described in example 1. Bleached material is treated as described in example 20 while distilled material is distilled as described in example 19.

Example 21

Enrichment of CLA by Crystallization in a Solvent Free System

Five hundred grams of fatty acid produced as described in example 1 was chilled to −20° C. and then warmed at 4° C. The chilling and thawing treatment resulted in the formation of persistent crystals that were readily removed from the fatty acids by filtration. The fatty acids were filtered over a chilled Buchner funnel at 4° C. One hundred and twenty five grams of fatty acid were retained on the filter while 375 grams passed through. The solid fatty acids retained on the filter contained a substantial amount of the desired CLA product. This product was substantially recovered by washing the solid fatty acids with 50 g of chilled sunflower oil. As the sunflower oil is substantially less valuable than the CLA product its loss in this procedure was acceptable. The final CLA product was further enriched by approximately 10% in total CLA content.

Example 22

Removal of PEG From CLA by Washing With Phosphoric Acid

Polyethylene glycol 300 (5 g) was dissolved in 100 grams of CLA rich oil produced as described in example 1 and the sample was heated and stirred in 50 mL water at 100° C. for 15 min. The PEG 300 content of upper CLA phase was determined by the method of Muir et al. 1998. It was found that substantial amounts of PEG were detectable in the CLA phase. The experiment was repeated in a similar manner except that the water was replaced with 50 mL of phosphoric acid and the mixture was stirred at 110° C. for 15 min. After the latter treatment PEG was not detected in the upper CLA rich phase.

Example 23

Synthesis of Deuterated CLA

Metallic sodium was added in portions under nitrogen to $D_2O$ (80 mL). The resulting NaOD solution was diluted to 100 mL with deuterated water to produce a 45% NaOD solution. To sunflower oil (140 mL) were added NaOD solution (100 mL) and $D_2O$ (20 mL). The reaction mixture was heated in a teflon lined stirred reactor at 210° C. for six hours. After cooling to room temperature, a portion of the reaction mixture (20 g) was acidified with H3PO4 (conc. 85%, 10 mL). Quebracho tannin (0.5 g) was added to the acidified mixture and the sample heated at 115° C. for 1.5 hour. After cooling to room temperature, the top CLA-D layer was separated, and deuterium exchange was determined by $^1H$ and $^{13}C$ NMR.

Figure 5:
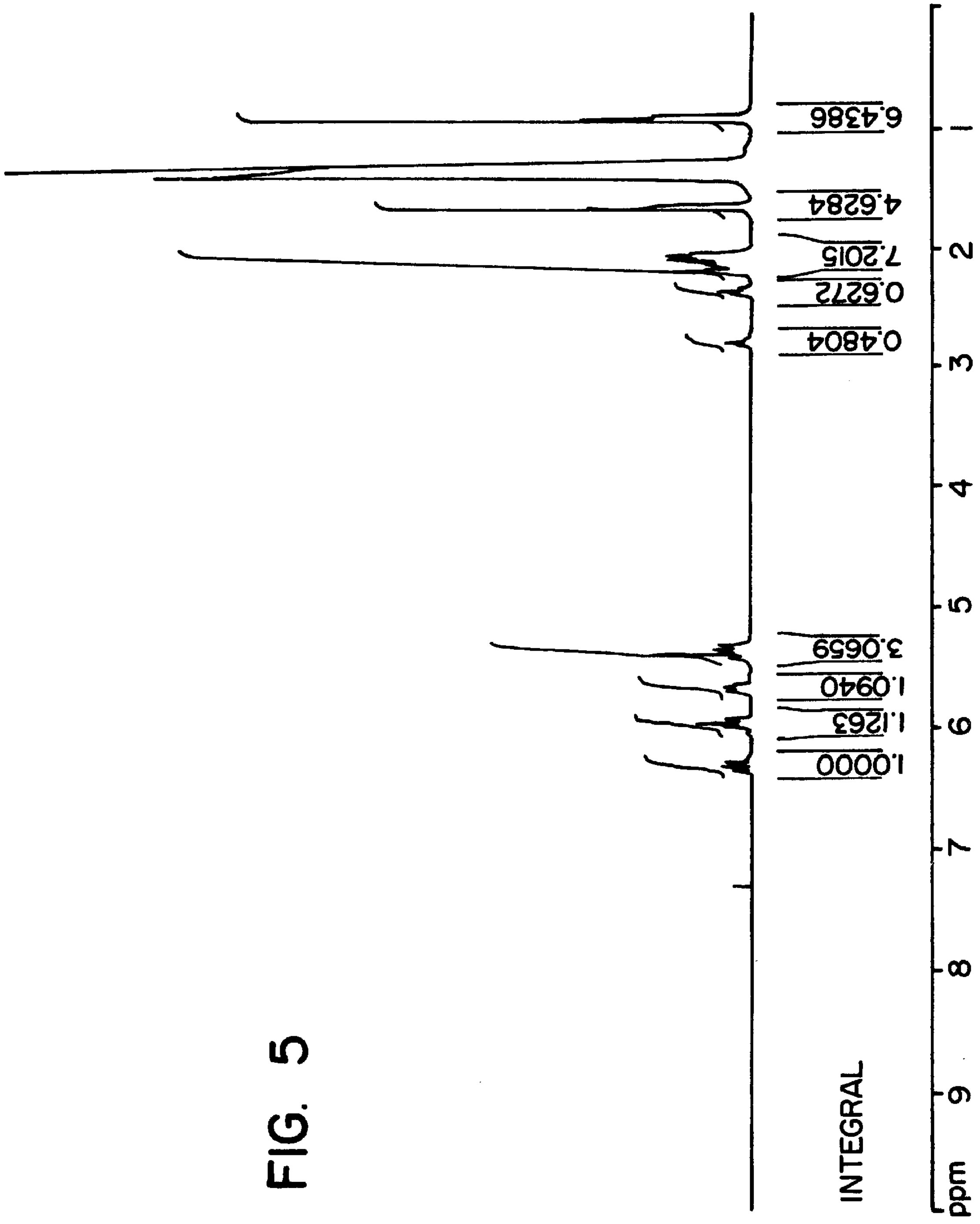
FIG. 5 is the proton spectrum of deuterated CLA.

Deuterium exchange of the beta carbon protons was detected by the decrease in the proton peak normally observed at 2.3 PPM (FIG. 5). Substitution of the protons on the carbon beta to the carbonyl was highly effective, as the relative area of the peak at 2.3 PPM should have been approximately the same as the peak observed at 1.7 PPM. The area observed was diminished by 86%. Protons that were adjacent to the trans bond in the conjugated diene system were also substituted during the reaction.

Example 24

Purification and Concentration of CLA by Crystallization

Conjugated linoleic acid prepared as described in example 1(22.3 g) was dissolved in 25 mL of acetone and the mixture was chilled to −18° C. where a solid precipitate was observed. The precipitate was removed by filtration and washed and weighed and the NMR spectrum recorded. The 2.5 g of recovered precipitate was found to contain primarily saturated fatty acids. The filtrate was diluted with a further 25 mL of acetone and then chilled to −60° C. whereupon a second white precipitate formed. The second precipitate was filtered at −60° C. and washed twice with acetone chilled to the same temperature. Solvent was evaporated from both phases and the weight and NMR spectra of each phase were recorded. The warmed crystals (15.1 g) melted to produce a clear solution enriched in conjugated fatty acids while the solution evaporated to yield 4.6 g of a clear but intensely yellow liquid.

Example 25

Production of a CLA Product Enriched in Trans, cis-10,12-octadecadienoic Acid

To sunflower oil (275 mL) were added KOH (210 mL @45%w/w), $Ca(OH)_2$ (32 g), water (110 mL). The reaction mixture was heated at 210° C. for five hours. After cooling to room temperature, a portion of the mixture (15 g) was acidified with $H_3PO_4$ (conc. 10 mL), water (30 mL) and Quebracho tannin (0.2 g) added. The resulting mixture was heated at 115° C. for two hours, and cooled to room temperature. The CLA containing layer was recorded on $^1H$ and $^{13}C$ The reaction products were found to contain 47 percent trans,cis-10,12-octadecadienoic acid and 31 percent cis,trans-9, 11-octadecadienoic acid. This novel isomer ratio has not been previously reported. Commercial CLA samples typically contain less than 30% CLA when measured by NMR.

Example 26

Simultaneous Hydrolysis and Isomerization of Sunflower Oil to CLA Followed by Washing, Dehydrating and Refining the CLA With Humic Acid or Fulvic Acid To commercial sunflower oil (275 mL) and water (121 mL) were added KOH (45% w/w, 204 mL). The resulting reaction mixture was heated at 215° C. (reactor pressure: 175 psi) for 6 hours in a one liter reactor with vigorous agitation. After cooling to room temperature, the reaction mixture was transferred to a two liter beaker, acidified with $H_3PO_4$ (85%, 204 mL), and 2 grams of fulvic acid or tannic acid added. The resulting mixture was heated for 2.5 h at 105–110° C. After standing for 0.5 hours 95° C., the top CLA layer was removed, washed with H3PO4 (85%, 30 mL), and heated at 95° C. for 30 minutes. The dried CLA layer was separated the treatments with either fulvic and humic acid initiated phase separation and 240 mL of CLA rich fatty acids were recovered from the reaction mixture.

What is claimed is:

1. A process for producing a conjugated linoleic acid-rich fatty acid mixture consisting essentially of: reacting a linoleic acid-rich oil containing hydrolysable acyl groups with a base, in the presence of a catalytic amount of said base, in an aqueous medium containing up to 100 moles of water per mole of said hydrolysable acyl groups at a temperature above 170° C., and after the reaction separating said conjugated linoleic acid-rich fatty acid mixture from said aqueous medium by cooling the reaction mixture to a temperature between about 90° and 100° C., treating the cooled reaction mixture with an acid so as to hydrolyse soaps therein, and separating the acidified reaction mixture into two phases by addition of a demulsifier selected from the group consisting of a tannin and a condensed tannin.

2. A process as claimed in claim 1, wherein said oil is a vegetable oil selected from the group consisting of cottonseed, cucumber, grapeseed, corn, safflower, soybean, sunflower, high linoleic acid flaxseed oil and walnut oil.

3. A process as claimed in claim 1, wherein said base is selected from the group consisting of sodium metal, sodium hydroxide, sodium alkoxylate, potassium metal, potassium hydroxide and potassium alkoxylate.

4. A process as claimed in claim 1 wherein pH of said cooled reaction mixture is reduced to less than pH 4.

5. A process as claimed in claim 4, wherein said acid is selected from the group consisting of hydrochloric, sulfuric, phosphoric and citric acid.

6. A process as claimed in claim 1, wherein said aqueous medium is selected from water, deuterated water, and triturated water.

7. A process as claimed in claim 6 wherein said temperature is in the range 170°–200° C.

8. A process as claimed in claim 1 wherein phosphoric acid is used to remove water from said fatty acid mixture.

9. A process for producing a conjugated linoleic acid-rich fatty acid mixture comprising: reacting a linoleic acid-rich oil containing hydrolysable acyl groups with a base, in the presence of a catalytic amount of said base, in an aqueous medium containing up to 100 moles of water per mole of said hydrolysable acyl groups at a temperature above 170° C., and after the reaction separating said conjugated linoleic acid-rich fatty acid mixture from said aqueous medium by cooling the reaction mixture to a temperature between about 90° and 100° C.; treating the cooled reaction mixture with an acid so as to hydrolyse soaps therein; and separating the acidified reaction mixture into two phases by addition of an acid selected from the group consisting of fulvic acid and humic acid.

10. A process as claimed in claim 8 wherein phosphoric acid is used to remove polyethylene glycol from said fatty acid mixture.

* * * * *